United States Patent [19]

Edamura

[11] 3,961,059

[45] June 1, 1976

[54] 6-(SUBSTITUTED PHENOXY)TETRAZOLO(1,5-b)PYRIDAZINES AND A METHOD OF USE FOR CONTROL OF SOIL-BORNE PLANT DISEASES

[75] Inventor: Fred Y. Edamura, Concord, Calif.

[73] Assignee: The Dow Chemical Company, Midland, Mich.

[22] Filed: May 1, 1975

[21] Appl. No.: 573,707

Related U.S. Application Data

[62] Division of Ser. No. 451,667, March 14, 1974, Pat. No. 3,914,228.

[52] U.S. Cl.............................. 424/250; 424/DIG. 8
[51] Int. Cl.$^2$........................................... A01N 9/22
[58] Field of Search....................... 424/250, DIG. 8

[56] References Cited

OTHER PUBLICATIONS

Takanobu et al., Chem. Abst. 59:8733–8736, 8734h.
Stonounik et al., Journal of Organic Chemistry 35, 1138–1141 (1970).

Primary Examiner—Jerome D. Goldberg
Assistant Examiner—Allen J. Robinson
Attorney, Agent, or Firm—S. Preston Jones; Gary D. Street; C. Kenneth Bjork

[57] ABSTRACT

Disclosed are novel 6-(substituted phenoxy)-tetrazolo(1,5-b)pyridazine compounds and methods employing the same for protecting plants from soil-borne disease both prior to infection and after infection by systemically killing and controlling the disease organisms.

8 Claims, No Drawings

6-(SUBSTITUTED PHENOXY)TETRAZOLO(1,5-B)PYRIDAZINES AND A METHOD OF USE FOR CONTROL OF SOIL-BORNE PLANT DISEASES

CROSS REFERENCE TO RELATED APPLICATION

This is a division, of application Ser. No. 451,667, filed Mar. 14, 1974, now U.S. Pat. No. 3,916,228, issued Oct. 21, 1975.

BACKGROUND OF THE INVENTION

The present invention relates to novel 6-(substituted phenoxy)tetrazolo(1,5-b)pyridazines and methods for controlling soil-borne disease organisms which attack plants.

The related prior art discloses 6-(4-methylphenyl)-tetrazolo(1,5-b)pyridazine and 6-(benzyloxy)-tetrazolo(1,5-b)pyridazine compounds. See Revue Roumaine di Chemie 10, 641 (1965), Chem. Abstr. 64:732h and Chem. Pharm. Bull. (Tokyo) 11, 348 (1963, Chem. Abstr. 59:8734h), respectively. The 6-(substituted phenoxy)tetrazolo(1,5-b)-pyridazines have not been previously described.

SUMMARY OF THE INVENTION

This invention relates to novel 6-(substituted phenoxy)tetrazolo(1,5-b)pyridazine compounds wherein the substituted phenoxy moiety is selected from the group consisting of 4-nitrophenoxy, 4-chlorophenoxy and 4-chloro-2-nitrophenoxy, such compounds being hereinafter referred to as "active ingredients". It has been found that the application of an effective amount of at least one of the active ingredients to plant life forms or their soil environment systemically protects the plant life forms against soil-bourne plant disease organisms.

In general, the compounds of the present invention are prepared by reacting 6-chlorotetrazolo(1,5-b)-pyridazine with a selected substituted phenol reactant. The reaction is usually carried out in the presence of an inert carrier solvent, such as acetonitrile, chloroform, benzene and similar solvents, and a base such as, for example, an alkali metal hydroxide or carbonate, such as potassium carbonate, sodium hydroxide and the like. The amounts of the reactants employed are not critical although substantially equimolar amounts of the reactants and base are usually employed. The reaction mixture is ordinarily heated at ambient pressure and under reflux conditions for periods of from about 2 to about 8 or more hours. Following the completion of the reaction, the reaction mixture is mixed with water and an appropriate solvent for extracting the desired compound, such as methylene dichloride, chloroform, carbon tetrachloride or the like. The extract can then be washed with water and base and evaporated to obtain the desired product as a crystalline solid.

In the present specification and claims, the term "plant" or "plant life form" is employed to designate all parts of a plant and includes seeds, seedlings, tuber, cutting, the root system, hereinafter commonly referred to as root, the crown, stalk, stem, foliage or leaf system, fruit or flower. As used herein, the terms "systemic" or "plant protectant" activity by an active ingredient refers to the assimilation and translocation of the chemical from the site of application into and through the vascular system of the plant whence it is distributed throughout the plant tissues, particularly in the underground portions of plants. Ovbiously, this is a complex process which is unpredictable, and is encountered much more infrequently than superficial or contact activity. Thus, if the active ingredient is applied to seeds, accumulation of the active compound is principally found in the underground system of the germinating seed; if applied to the above ground portions of the plant life form or to the environment thereof, e.g., soil, the active ingredient generally translocates and principally accumulates in the underground portion of the plant.

Representative soil-borne plant disease organisms which are known to attack the below ground portion of plants include *Verticillium*, *Rhizoctonia*, *Phytophthora*, *Pythium* and *Thielaviopsis*. Of these, water mold disease organisms such as *Pythium* and *Phytophthora* are believed to be the principal disease problems for desirable plants; the active ingredients employed herein are particularly effective against *Phytophthora*. The present invention thus is useful in providing for the control of the various soil-borne diseases which are known to attack a variety of plants, such as, for example, cereal crops, such as, corn, wheat, barley, rice and sorghum; truck crops, such as, cucurbits (melons, cucumbers, squash, etc.), crucifiers (cabbage, broccoli, etc.), tomatoes and peppers; legumes, such as, peanuts, soybeans, beans, peas, and alfalfa; other crops, such as, tobacco, potatoes, cotton, sugar beets and pineapple; perennial crops, particularly in the seedling stage, such as, citrus (orange, lemon, grapefruit, etc.), apples, pears, peaches, cherries, nut crops (walnuts, pecans, almonds, etc.), grapes, avocado; non-food grass species commonly referred to as turf and nursery and ornamental crops, such as, chrysanthemums, azaleas, rhododendrons, violets, carnations, lilies and shade and foliage ornamentals, such as, philodendrons, Schefflera and Dieffenbachia and the like and gymnosperms such as pine, Arborvitae, spruce, junipers and the like.

Plant-protecting amounts of an active ingredient is conveniently applied to plants and/or plant environment, e.g., soil, either before or after the plant has been attacked by soil-borne plant disease organisms, by procedures such as soil injection, drenching with an aqueous composition, seed treatment, topical spraying, furrow spraying or other techniques known to those skilled in the art. The only limitation upon the mode of application employed, is that is must be one which will place the toxicant in direct contact with seeds or plant parts.

The exact dosage of the active ingredient employed will vary depending upon the specific plant, hardiness of the plant, nature of the soil and mode of application. Generally, for practical applications on a commercial scale, the active ingredient can be broadly applied at application rates of from about 0.1 to about 5.0 pounds or more on a per acre basis. Amounts of various diluted solutions containing the active ingredient in terms of parts per million (ppm) necessary to achieve a desired application rate can readily be determined by those skilled in the art given the active ingredient concentration. For example, the application of 200 gallons of a solution containing 600 ppm active ingredient is generally equivalent to the application of about one pound of active ingredient per acre. A preferred range is from about ¼ to about 3.0 or more pounds per acre. Commercially, seed treatments are customarily recommended on the basis of ounces per hundredweight per bushel. This can be expressed in ppm as from about 5.0 to about 1000 ppm or more. The upper limit in any of the foregoing application rates is, of course, determined by phytotoxic manifestations encountered by the treatment, which will depend upon the compound employed and the various factors set forth above. Of course, lesser or greater rates can be utilized depending upon the particular situation.

Larger amounts of the active ingredient advantageously may be applied when treatments are employed which distribute the material throughout the soil. For example, when the active ingredient is applied as an at-plant row treatment or as an early season post-plant side-dress treatment, those amounts of chemical not proximal to plant roots are essentially unavailable to the plant and therefore not effective as set forth hereinabove. In such practices, amounts of the active ingredient need to be increased to rates as high as about 10 pounds or more per acre to assure the requisite effective quantity of active ingredient is made available to the plants.

The present invention can be carried out by employing the active ingredients directly, either singly or in combination. However, the present invention also embraces the employment of liquids, dusts, wettable powders, granules or encapsulated compositions containing at least one of said compounds as active ingredient. In such usage, the compound or compounds can be modified with one or more of a plurality of inert solid or liquid carrier adjuvants including inert solvents, inert liquid carriers and/or surface active dispersing agents and coarsely or finely divided inert solids. The augmented compositions are also adapted to be employed as concentrates and subsequently diluted with additional inert carrier to produce other compositions in the form of dusts, sprays, granules, washers or drenches. In compositions where the adjuvant is a coarsely or finely divided solid, a surface active agent or the combination of a surface active agent and a liquid additament, the adjuvant cooperates with the active component so as to facilitate the invention. Whether the composition is employed in liquid, wettable powder, dust, granule or encapsulated form, the active compound will normally be present in an amount of from about 2 to 98 percent by weight of the total composition.

In the preparation of dust, or wettable powder compositions, the active ingredient can be compounded with any of the finely divided solids, such as pyrophyllite, talc, chalk, gypsum, fuller's earth, bentonite, attapulgite, starch, casein, gluten and the like. In such operations, the finely divided carrier is ground or mixed with the toxicant or wet with a solution of the active ingredient in a volatile organic solvent. Also, such compositions when employed as concentrates can be dispersed in water, with or without the aid of dispersing agents to form spray mixtures.

Granular formulations are usually prepared by impregnating a solution of the active ingredient in a volatile organic solvent onto a bed of coarsely divided attapulgite, bentonite, diatomite, or the like.

Similarly, the active ingredient can be compounded with a suitable water-immiscible inert organic liquid and a surface active dispersing agent to produce an emulsifiable concentrate which can be further diluted with water and oil to form spray mixtures in the form of oil-in-water emulsions. In such compositions, the carrier comprises an aqueous emulsion, i.e., a mixture of inert water-immiscible solvent, emulsifying agent and water. Preferred dispersing agents which can be employed in these compositions, are oil-soluble materials including non-ionic emulsifiers such as the condensation products of alkylene oxides with the inorganic acids, polyoxyethylene derivatives or sorbitan esters, complex ether alcohols and the like. Also, oil-soluble ionic emulsifying agents such as mahogany soaps can be used. Suitable inert organic liquids which can be employed in the compositions include petroleum oils and distillates, toluene, liquid halohydrocarbons and synthetic organic oils. The surface-active dispersing agents are usually employed in liquid compositions and in the amount of from 0.1 to 20 percent by weight of the combined weight of the dispersing agent and active ingredient.

In addition, other liquid compositions containing the desired amount of active ingredient can be prepared by dissolving the same in an inert organic liquid such as acetone, methylene chloride, chlorobenzene and petroleum distillates. The preferred inert organic solvent carriers are those which are adapted to accomplish the penetration and impregnation of the environment and particularly soil with the toxicant compounds and are of such volatility as to leave little permanent residue thereon. Particularly desirable carriers are the petroleum distillates boiling almost entirely under 400°F. at atmospheric pressure and having a flash point above 80°C. The proportion of the compounds of this invention employed in a suitable solvent may vary from about 2 to about 50 percent or higher.

A preferred liquid composition includes the use of the active ingredient or ingredients in combination with surface active dispersant agents only. In such compositions, it is preferred to use ionic and non-ionic blends of such dispersant agents in combination with one or more of the active materials. A particular advantage of such a formation is that phytotoxicity associated with certain inert solvents, such as, xylene, methylene chloride, and like materials can be avoided. Generally, the use of such formulations will result in compositions containing 75 percent or more of the active component.

Owing to the excellent suspensibility of the above formulation in water, it is convenient and often preferred to prepare and use aqueous concentrates as stock solutions themselves. In such practices, minor agitation results in a practical, stable formulation very adaptable for use in its concentrate form to treat soil in sprays or drenches. Additionally, if desired, the concentrates can be easily diluted with additional water for use as foliar spray treatments, soil drench treatments and the like.

Water miscible organic solvents such as lower alcohols or propylene glycol can be added to depress the freezing point and further cooperate with the above system in that they are essentially non-phytotoxic.

DESCRIPTION OF THE PREFERRED EMBODIMENTS

In order that the present invention may be more fully understood, the following examples are provided to illustrate the manner by which it can be practiced but, as such should not be construed as limitations upon the overall scope of the same.

Example 1

6-Chlorotetrazolo(1,5-b)pyridazine (7.5 grams; 0.046 mole), (prepared from 3,6-dichloropyridazine according to N. Takahayashi, J. Pharm. Soc. Japan, 75, 1242 (1955); Chem. Abstr. 50, 8656) was mixed with p-nitrophenol (7.4 grams; 0.053 mole) and potassium carbonate (7.4 grams, 0.053 mole) in 100 milliliters (ml) of acetonitrile and the resulting reaction mixture heated under reflux conditions for a period of about four hours. Following the reaction period, the reaction mixture was mixed with 100 ml of water and 100 ml of methylene chloride. The organic layer was separated and the remaining aqueous layer further extracted with four-50 ml portions of methylene chloride. The organic extracts were combined and the mixture washed successively with a 5 percent solution of sodium hydroxide and water. The mixture was then dried and evaporated to obtain the desired product which was recrystallized from methylene chloride. As a result of such operations, the desired 6-(4-nitrophenoxy)tetrazolo(1,5-b)pyridazine (hereinafter, compound A) was obtained as a crystalline solid having a melting point of 207°C.

6-(4-chlorophenoxy)tetrazolo(1,5-b)pyridazine (hereinafter, compound B), having a melting point of 185°–186°C., was similarly obtained according to the procedure of Example 1 by employing p-chlorophenol in place of p-nitro-phenol. Likewise, 6-(4-chloro-2-nitrophenoxy)tetrazolo(1,5-b)pyridazine (hereinafter, compound C) having a melting point of 219°–221°C., was obtained according to Example 1 using 4-chloro-2-nitrophenol in place of p-nitrophenol.

Example 2

10,000 ppm concentrate solutions of each of compounds A, B and C were prepared in acetone and appropriate portions of each concentrate were added to 100 ml of water to prepare separate treating compositions containing 100 and 25 ppm of each active ingredient. Soil infected with tobacco black shank, pathogen Phytophthora parasitica var. nicotiane was placed in a predetermined number of 2-inch pots and small, 3 to 4 week old tobacco seedlings, grown in a disease-free medium, were transplanted into such pots. Immediately after transplanting, sets of pots were drenched with 40 ml of one of the treating compositions. The treated pots, along with untreated controls, were then maintained under conditions conducive to growth and watered daily. About one week after the tests were started, the untreated controls were dead and the treated plants were evaluated for disease control. As a result of such operations, it was found that each of test compounds A, B and C gave 100 percent control of the tobacco black shank disease organisms at each test concentration.

While several particular embodiments of this invention are shown above, it will be understood, of course, that the invention is not to be limited thereto, since many modifications may be made, and it is contemplated, therefore, by the appended claims, to cover any such modifications as fall within the true spirit and scope of this invention.

What is claimed:

1. A method for controlling plant diseases selected from the group consisting of Verticillium, Rhizoctonia, Phytophthora, Pythium, and Thielaviopsis on plants or soil thereof which comprises applying to said plants or soil an effective amount for controlling plant diseases of a 6-(substituted phenoxy) tetrazolo (1, 5-b)-pyridazine compound wherein said substituted phenoxy moiety is selected from the group consisting of 4-nitrophenoxy, 4-chlorophenoxy and 4-chloro-2-nitrophenoxy.

2. The method of claim 1 wherein said plants or soil are contacted with said pyridazine compound prior to being attacked by said plant diseases.

3. The method of claim 1 wherein said plants or soil are contacted with said pyridazine compound after being attacked by said plant diseases.

4. The method of claim 1 wherein said pyridazine compound is employed in combination with an inert carrier.

5. The method of claim 1 wherein said pyridazine compound is 6-(4-nitrophenoxy)tetrazolo(1,5-b)pyridazine.

6. The method of claim 1 wherein said pyridazine compound is 6-(4-chlorophenoxy)tetrazolo(1,5-b)pyridazine.

7. The method of claim 1 wherein said pyridazine compound is 6-(4-chloro-2-nitrophenoxy)tetrazolo(1,5-b)-pyridazine.

8. The method of claim 1 wherein said pyridazine compound is employed at a rate of from about 0.1 to about 5.0 pounds per acre.

* * * * *